US012788329B2

(12) United States Patent
Verma et al.

(10) Patent No.: US 12,788,329 B2
(45) Date of Patent: Nov. 10, 2026

(54) TECHNIQUES FOR MEASURING HEART RATE ANALYTICS FROM PHOTOPLETHYSMOGRAPHY DATA THAT ARE ROBUST TO MOTION ARTIFACTS

(71) Applicant: Verily Health Inc., Dallas, TX (US)

(72) Inventors: Nishant Verma, Cary, NC (US); Charles Mathy, Boston, MA (US); Miles Bennett, San Bruno, CA (US); Akshaya Vagula Booshanam, San Bruno, CA (US)

(73) Assignee: Verily Health Inc., Dallas, TX (US)

( * ) Notice: Subject to any disclaimer, the term of this patent is extended or adjusted under 35 U.S.C. 154(b) by 0 days.

(21) Appl. No.: 19/215,151

(22) Filed: May 21, 2025

(65) Prior Publication Data

US 2025/0366789 A1 Dec. 4, 2025

Related U.S. Application Data

(60) Provisional application No. 63/653,444, filed on May 30, 2024.

(51) Int. Cl.
*A61B 5/00* (2006.01)
*A61B 5/024* (2006.01)

(52) U.S. Cl.
CPC ........ *A61B 5/7207* (2013.01); *A61B 5/02405* (2013.01); *A61B 5/02416* (2013.01);
(Continued)

(58) Field of Classification Search
CPC ..................................................... A61B 5/7207
See application file for complete search history.

(56) References Cited

U.S. PATENT DOCUMENTS

2014/0275854 A1 9/2014 Venkatraman et al.
2014/0275889 A1 9/2014 Addison et al.
(Continued)

OTHER PUBLICATIONS

Sadhukhan, D., et al., "PPG Noise Reduction based on Adaptive Frequency Suppression using Discrete Fourier Transform for Portable Home Monitoring Applications", 2018 15th IEEE India Council International Conference (INDICON), Dec. 16-18, 2018, 7 pages.

(Continued)

*Primary Examiner* — Joseph M Santos Rodriguez
(74) *Attorney, Agent, or Firm* — Christensen O'Connor Johnson Kindness PLLC

(57) ABSTRACT

In some embodiments, a computer-implemented method of measuring heart rate analytics using raw photoplethysmography (PPG) data is provided. A computing system determines a plurality of frequency peaks in the raw PPG data using a Fourier analysis. The computing system determines a plurality of selected frequency peaks from the plurality of frequency peaks. For each selected frequency peak of the plurality of selected frequency peaks, the computing system creates filtered PPG data by applying a frequency of the selected frequency peak as a high-pass filter to the raw PPG data; detects diastole peaks and systole valleys in the filtered PPG data; and performs one or more pulse quality checks on the detected diastole peaks and systole valleys. The computing system uses diastole peaks and systole valleys associated with a lowest selected frequency peak that passed the pulse quality checks to determine a heart rate analytic measurement.

14 Claims, 8 Drawing Sheets

(52) U.S. Cl.
CPC .......... *A61B 5/02438* (2013.01); *A61B 5/725* (2013.01); *A61B 5/7257* (2013.01)

(56) References Cited

U.S. PATENT DOCUMENTS

| | | | |
|---|---|---|---|
| 2016/0317096 | A1 | 11/2016 | Adams et al. |
| 2018/0279891 | A1 | 10/2018 | Miao et al. |
| 2019/0298195 | A1 | 10/2019 | De Groot et al. |
| 2019/0332757 | A1 | 10/2019 | Chen et al. |
| 2021/0113104 | A1 | 4/2021 | Firoozabadi et al. |
| 2021/0212582 | A1 | 7/2021 | Fathieh et al. |
| 2022/0133161 | A1 | 5/2022 | Jones et al. |
| 2022/0183608 | A1 | 6/2022 | Zhu et al. |

OTHER PUBLICATIONS

Kleiger, R.E., et al., Heart Rate Variability: Measurement and Clinical Utility, Annals of Noninvasive Electrocardiology, vol. 10, No. 1, Jan. 13, 2005, pp. 88-101.
PCT International Search Report and Written Opinion mailed Aug. 1, 2025, in corresponding International application No. PCT/US2025/030576, 10 pages.

TECHNIQUES FOR MEASURING HEART RATE ANALYTICS FROM PHOTOPLETHYSMOGRAPHY DATA THAT ARE ROBUST TO MOTION ARTIFACTS

CROSS-REFERENCE(S) TO RELATED APPLICATION(S)

This application claims the benefit of Provisional Application No. 63/653,444, filed May 30, 2024, the entire disclosure of which is hereby incorporated by reference herein for all purposes.

TECHNICAL FIELD

This disclosure relates generally to heart monitoring, and in particular but not exclusively, relates to using photoplethysmography for heart monitoring.

BACKGROUND

Photoplethysmography (PPG) is a monitoring technique in which blood flow is measured based on an amount of light absorbed by the blood vessels under the skin. PPG data is frequently generated by wearable sensor devices, including but not limited to wrist or finger mounted sensor devices, which measure blood volume in a peripheral part of the body. With each cardiac cycle, the heart pumps blood to the periphery, and changes the blood volume in the periphery. These changes can be measured within PPG data, where each cardiac cycle manifests as a peak and a valley. Accordingly, PPG data may be used to automatically measure clinically meaningful heart rhythm metrics including but not limited to heart rate and heart rate variability that can be used for both wellness and clinical purposes. Since PPG data can be collected with widely available, inexpensive, minimally invasive sensors, being able to use PPG data for clinically relevant measurements is highly desirable to increase access to high-quality diagnosis and care.

Unfortunately, designing automated systems to analyze PPG data and extract clinically relevant measurements is far from trivial. For example, PPG data is highly sensitive to motion artifacts, even when induced by low-amplitude motion such as finger movement. As another example, PPG data is also sensitive to morphological characteristics, such as reflection waves of blood pressure changes initiated by heartbeats. Such reflection waves are increasingly prevalent when collecting PPG data from a peripheral body part such as a finger or wrist.

FIG. 1 is a chart that shows a segment of simulated raw PPG data that includes confounding artifacts. The raw PPG data includes a plurality of peaks and valleys. Some peaks and valleys, such as peak 102 and valley 104, accurately represent a diastolic peak and systolic valley, respectively, of a heartbeat. However, other peaks and valleys, such as peak 106 and valley 108, are spurious peaks observed from the pressure change initiated at the heart reflecting off of, for example, a subject's pelvis. These reflected signals are often improperly identified as representing diastolic peaks and systolic valleys of heartbeats by previous techniques. Further, since these reflected signals are caused by the morphological features of the subject regardless of the presence of motion, it is not possible to avoid these artifacts using motion detection techniques.

These sensitivities make reliable detection of heartbeats in PPG data alone a challenging task. While heart rate measurements may be relatively forgiving to small errors made in heart beat detection, other clinically relevant measurements such as heart rate variability may be very sensitive to missed heartbeats or false heartbeats detected in the signal. Therefore, automated techniques are desired that accurately measure both heart rate and heart rate variability using PPG data that are robust to motion artifacts and the presence of confounding morphological features that arise when gathering PPG data from a sensor applied to a peripheral body part.

A variety of techniques have been proposed to overcome these difficulties, but none have been successful. One commonly used pre-processing step is to use a pre-specified frequency cutoff for filtering out low frequency confounders (such as respiration) from the PPG data. However, in the presence of motion artifacts, such frequency cutoffs are ineffective, and contributions unrelated to the heartbeat persist in the filtered signal and affect downstream heartbeat detection. Further, previously proposed techniques may also not be robust to physiological changes because of the lack of separation of frequencies between the different periodic confounding signals that may affect the PPG data, such as from respiration or periodic motion. For example, a frequency of 0.5 Hz could correspond to a heartbeat, a respiration signal, or a frequency at which a subject swings their arms while running or walking. As a result, such static methods may continue to produce unreliable and noisy estimates of heartbeat metrics.

BRIEF SUMMARY

In some embodiments, a non-transitory computer-readable medium having logic stored thereon is provided. The logic, in response to execution by one or more processors of a computing system, causes the computing system to perform actions for measuring heart rate analytics using raw photoplethysmography (PPG) data, the actions comprising: determining, by the computing system, a plurality of frequency peaks in the raw PPG data using a Fourier analysis; determining, by the computing system, a plurality of selected frequency peaks from the plurality of frequency peaks; for each selected frequency peak of the plurality of selected frequency peaks: creating, by the computing system, filtered PPG data by applying a frequency of the selected frequency peak as a high-pass filter to the raw PPG data; detecting, by the computing system, diastole peaks and systole valleys in the filtered PPG data; and performing, by the computing system, one or more pulse quality checks on the detected diastole peaks and systole valleys; and using, by the computing system, diastole peaks and systole valleys associated with a lowest selected frequency peak that passed the pulse quality checks to determine a heart rate analytic measurement.

In some embodiments, a computer-implemented method of measuring heart rate analytics using raw photoplethysmography (PPG) data is provided. A computing system determines a plurality of frequency peaks in the raw PPG data using a Fourier analysis. The computing system determines a plurality of selected frequency peaks from the plurality of frequency peaks. For each selected frequency peak of the plurality of selected frequency peaks, the computing system creates filtered PPG data by applying a frequency of the selected frequency peak as a high-pass filter to the raw PPG data; detects diastole peaks and systole valleys in the filtered PPG data; and performs one or more pulse quality checks on the detected diastole peaks and systole valleys. The computing system uses diastole peaks and systole valleys associated with a lowest selected frequency peak that passed the pulse quality checks to determine a heart rate analytic measurement.

BRIEF DESCRIPTION OF THE SEVERAL VIEWS OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described. To easily identify the discussion of any particular element or act, the most significant digit or digits in a reference number refer to the figure number in which that element is first introduced.

DETAILED DESCRIPTION

In embodiments of the present disclosure, techniques are used that accurately detect heartbeats in raw PPG data collected from wearable PPG sensors configured to collect data from peripheral body parts of a subject. The techniques are robust even to subtle periodic motion artifacts, and also compensate for reflected signals. Further, since the techniques use thresholds based on physiological characteristics, the techniques work on raw PPG data collected with a variety of different sensors, and with sensors worn in different locations.

Figure 1:
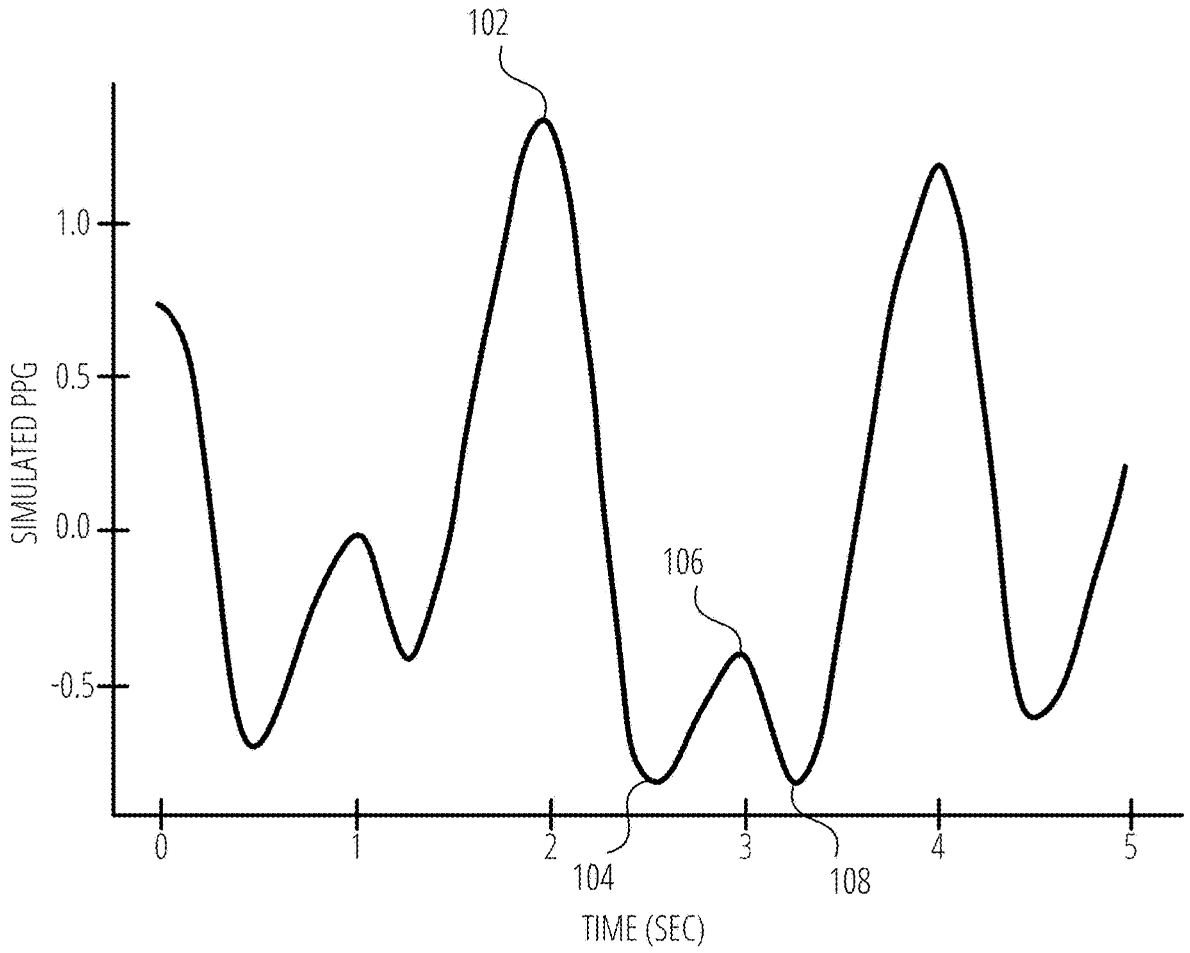
FIG. 1 is a chart that shows a segment of simulated raw PPG data that includes confounding artifacts.
Figure 2:
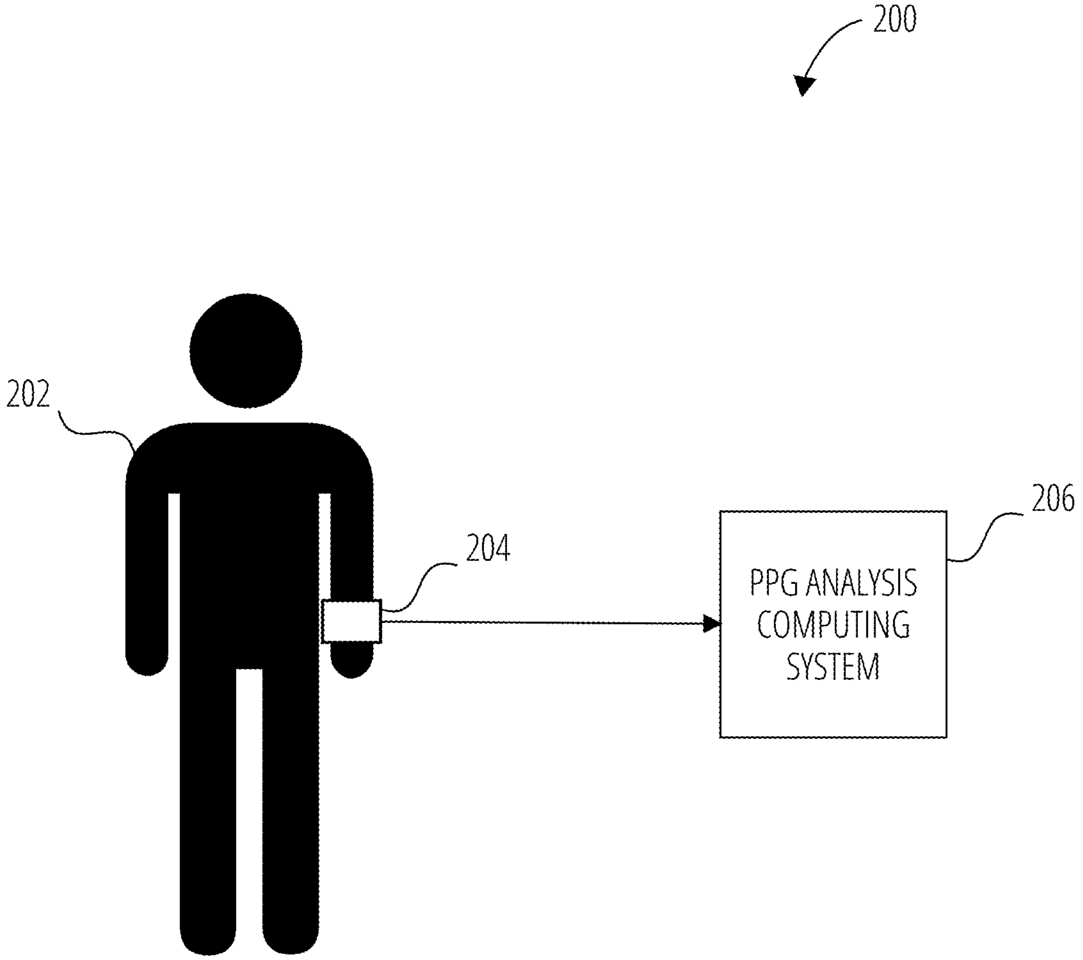
FIG. 2 is a schematic diagram of a system for measuring heartbeat characteristics of a subject using PPG data according to various aspects of the present disclosure.

FIG. 2 is a schematic diagram of a system for measuring heartbeat characteristics of a subject using PPG data according to various aspects of the present disclosure. As illustrated, the system 200 includes a wearable PPG sensor 204. The wearable PPG sensor 204 is worn by a subject 202, which is illustrated as a human.

The wearable PPG sensor 204 may take any suitable form factor. For example, the wearable PPG sensor 204 may be a minimally intrusive sensor, such as a sensor coupled to a wrist strap (as with a smart watch or other watch-like device) or a finger-worn ring. Other examples of wearable PPG sensors 204 may also be used, including but not limited to a clip applied to a fingertip or an earlobe, an ankle bracelet, a headband, or a chest strap. As known to those of ordinary skill in the art, a typical wearable PPG sensor 204 includes a light source that emits light toward the subject 202, and a photodetector that measures the light reflected from a tissue of the subject 202. In some embodiments, the wearable PPG sensor 204 may be integrated into a device that includes other sensors, including but not limited to microphones, motion sensors, or ambient light sensors.

The wearable PPG sensor 204 generates raw PPG data based on blood circulation of the subject 202. In some embodiments, the wearable PPG sensor 204 transmits the raw PPG data to a PPG analysis computing system 206, which in turn analyzes the raw PPG data to detect heart beats and calculate various metrics based thereon. In some embodiments, the wearable PPG sensor 204 may transmit the raw PPG data to the PPG analysis computing system 206 via one or more wired or wireless communication technologies, including but not limited to Bluetooth, Wi-Fi, USB, Fire Wire, or other technologies. In some embodiments, the wearable PPG sensor 204 may store the raw PPG data for several hours, days, or other amount of time prior to transmission to the PPG analysis computing system 206 or another device. In some embodiments, the wearable PPG sensor 204 may transmit the raw PPG data to the PPG analysis computing system 206 via one or more intermediate devices, including but not limited to a smartphone or other communication device paired with the wearable PPG sensor 204 and communicatively coupled to the PPG analysis computing system 206. In some embodiments, instead of transmitting the raw PPG data to the PPG analysis computing system 206, components of the PPG analysis computing system 206 may be integrated into the device that includes the wearable PPG sensor 204, such that the detection and analysis of heart beats may be performed by the device that includes the wearable PPG sensor 204.

Figure 3:
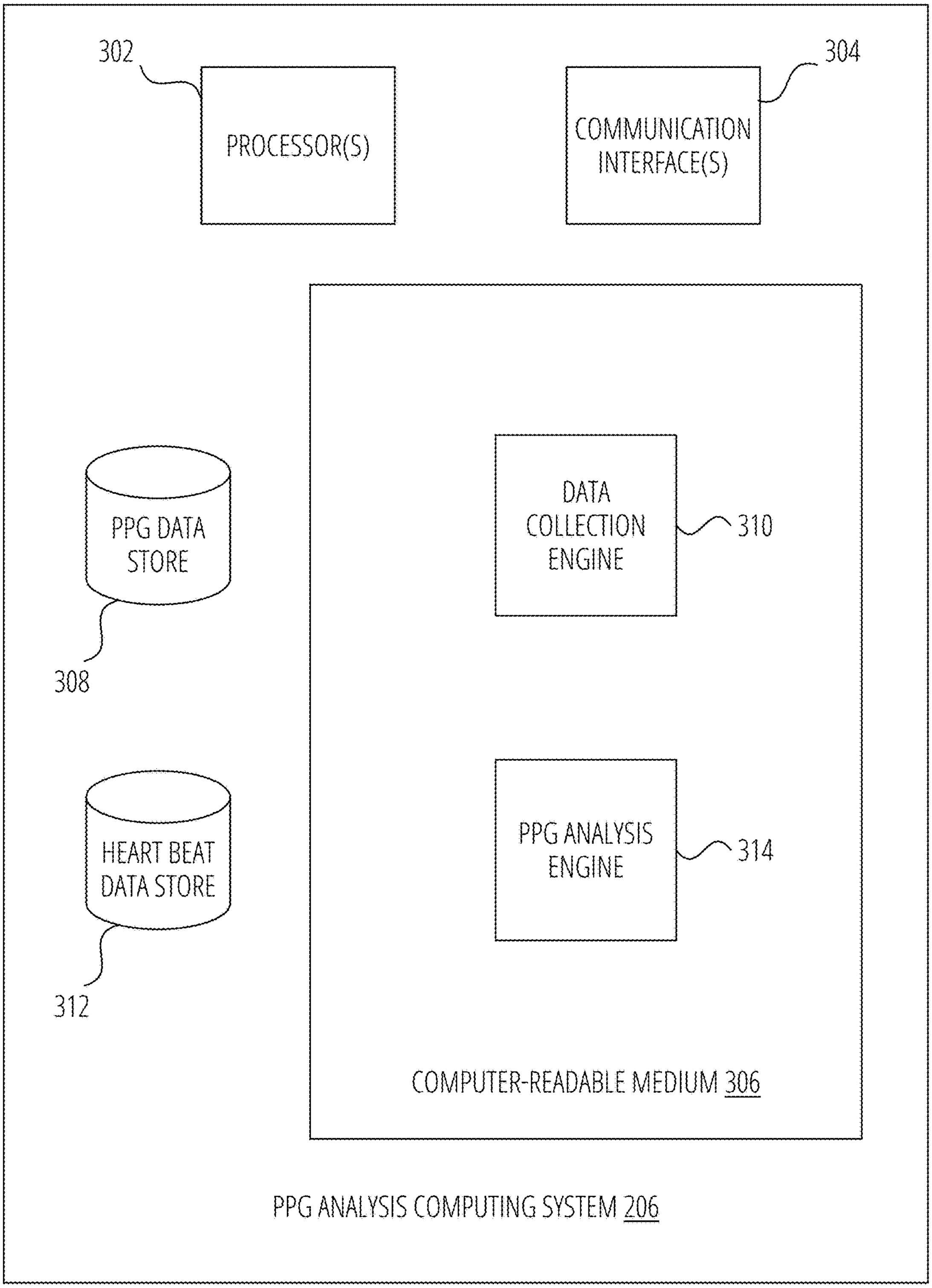
FIG. 3 is a block diagram that illustrates a non-limiting example embodiment of a PPG analysis computing system according to various aspects of the present disclosure.

FIG. 3 is a block diagram that illustrates a non-limiting example embodiment of a PPG analysis computing system according to various aspects of the present disclosure. The illustrated PPG analysis computing system 206 may be implemented by any computing device or collection of multiple computing devices, including but not limited to one or more desktop computing devices, laptop computing devices, mobile computing devices, server computing devices, computing devices of a cloud computing system, and/or combinations thereof. The PPG analysis computing system 206 is configured to receive raw PPG data from a wearable PPG sensor 204, to determine accurate heart beat information from the raw PPG data regardless of the type of wearable PPG sensor 204 and despite the presence of motion and reflectance artifacts, from which clinical measurements related to the heart beat information may reliably be calculated.

As shown, the PPG analysis computing system 206 includes one or more processors 302, one or more communication interfaces 304, a PPG data store 308, a heart beat data store 312, and a computer-readable medium 306.

In some embodiments, the processors 302 may include any suitable type of general-purpose computer processor. In some embodiments, the processors 302 may include one or more special-purpose computer processors or AI accelerators optimized for specific computing tasks, including but not limited to graphical processing units (GPUs), vision processing units (VPUs), and tensor processing units (TPUs).

In some embodiments, the communication interfaces 304 include one or more hardware and or software interfaces suitable for providing communication links between components. The communication interfaces 304 may support one or more wired communication technologies (including but not limited to Ethernet, Fire Wire, and USB), one or more wireless communication technologies (including but not limited to Wi-Fi, WiMAX, Bluetooth, 2G, 3G, 4G, 5G, and LTE), and/or combinations thereof.

As shown, the computer-readable medium 306 has stored thereon logic that, in response to execution by the one or more processors 302, cause the PPG analysis computing system 206 to provide a data collection engine 310, and a PPG analysis engine 314.

In some embodiments, the data collection engine 310 is configured to receive the raw PPG data from one or more wearable PPG sensors 204 and to store the raw PPG data in the PPG data store 308. In some embodiments, the PPG analysis engine 314 is configured to read the raw PPG data from the PPG data store 308, determine heart beat data based on the raw PPG data, and store the heart beat data in the heart beat data store 312. The PPG analysis engine 314 may also determine various metrics based on the heart beat data. Further description of the configuration of each of these components is provided below.

As used herein, "engine" refers to logic embodied in hardware or software instructions, which can be written in one or more programming languages, including but not limited to C, C++, C #, COBOL, JAVA™, PHP, Perl, HTML, CSS, JavaScript, VBScript, ASPX, Go, and Python. An engine may be compiled into executable programs or written in interpreted programming languages. Software engines may be callable from other engines or from themselves. Generally, the engines described herein refer to logical modules that can be merged with other engines, or can be divided into sub-engines. The engines can be implemented by logic stored in any type of computer-readable medium or computer storage device and be stored on and executed by one or more general purpose computers, thus creating a special purpose computer configured to provide the engine or the functionality thereof. The engines can be implemented by logic programmed into an application-specific integrated circuit (ASIC), a field-programmable gate array (FPGA), or another hardware device.

As used herein, "computer-readable medium" refers to a removable or nonremovable device that implements any technology capable of storing information in a volatile or non-volatile manner to be read by a processor of a computing device, including but not limited to: a hard drive; a flash memory; a solid state drive; random-access memory (RAM); read-only memory (ROM); a CD-ROM, a DVD, or other disk storage; a magnetic cassette; a magnetic tape; and a magnetic disk storage.

As used herein, "data store" refers to any suitable device configured to store data for access by a computing device. One example of a data store is a highly reliable, high-speed relational database management system (DBMS) executing on one or more computing devices and accessible over a high-speed network. Another example of a data store is a key-value store. However, any other suitable storage technique and/or device capable of quickly and reliably providing the stored data in response to queries may be used, and the computing device may be accessible locally instead of over a network, or may be provided as a cloud-based service. A data store may also include data stored in an organized manner on a computer-readable storage medium, such as a hard disk drive, a flash memory, RAM, ROM, or any other type of computer-readable storage medium. One of ordinary skill in the art will recognize that separate data stores described herein may be combined into a single data store, and/or a single data store described herein may be separated into multiple data stores, without departing from the scope of the present disclosure.

Figure 4A:
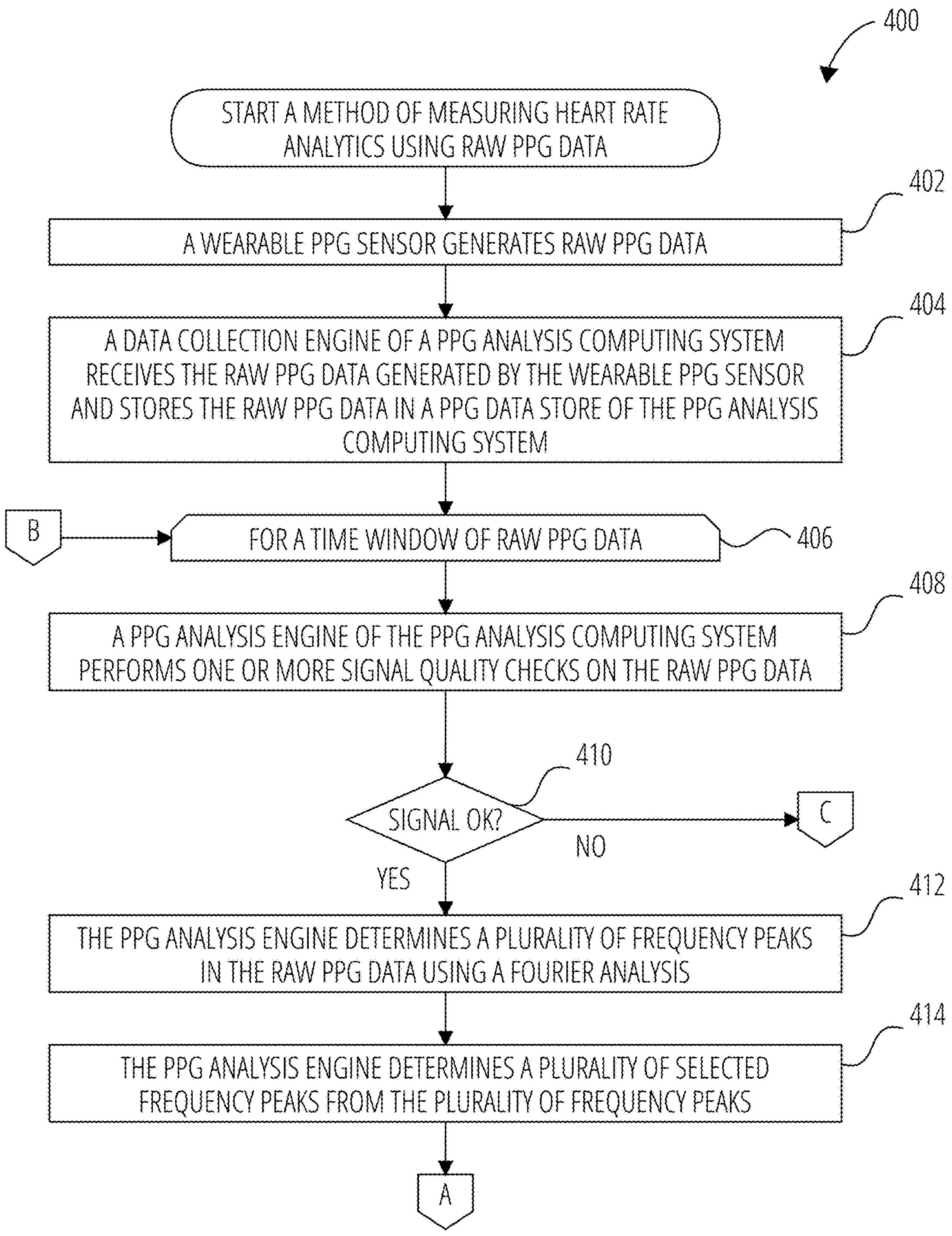
FIG. 4A-FIG. 4B are a flowchart that illustrates a non-limiting example embodiment of a method of measuring heart rate analytics using raw PPG data according to various aspects of the present disclosure.
Figure 4B:
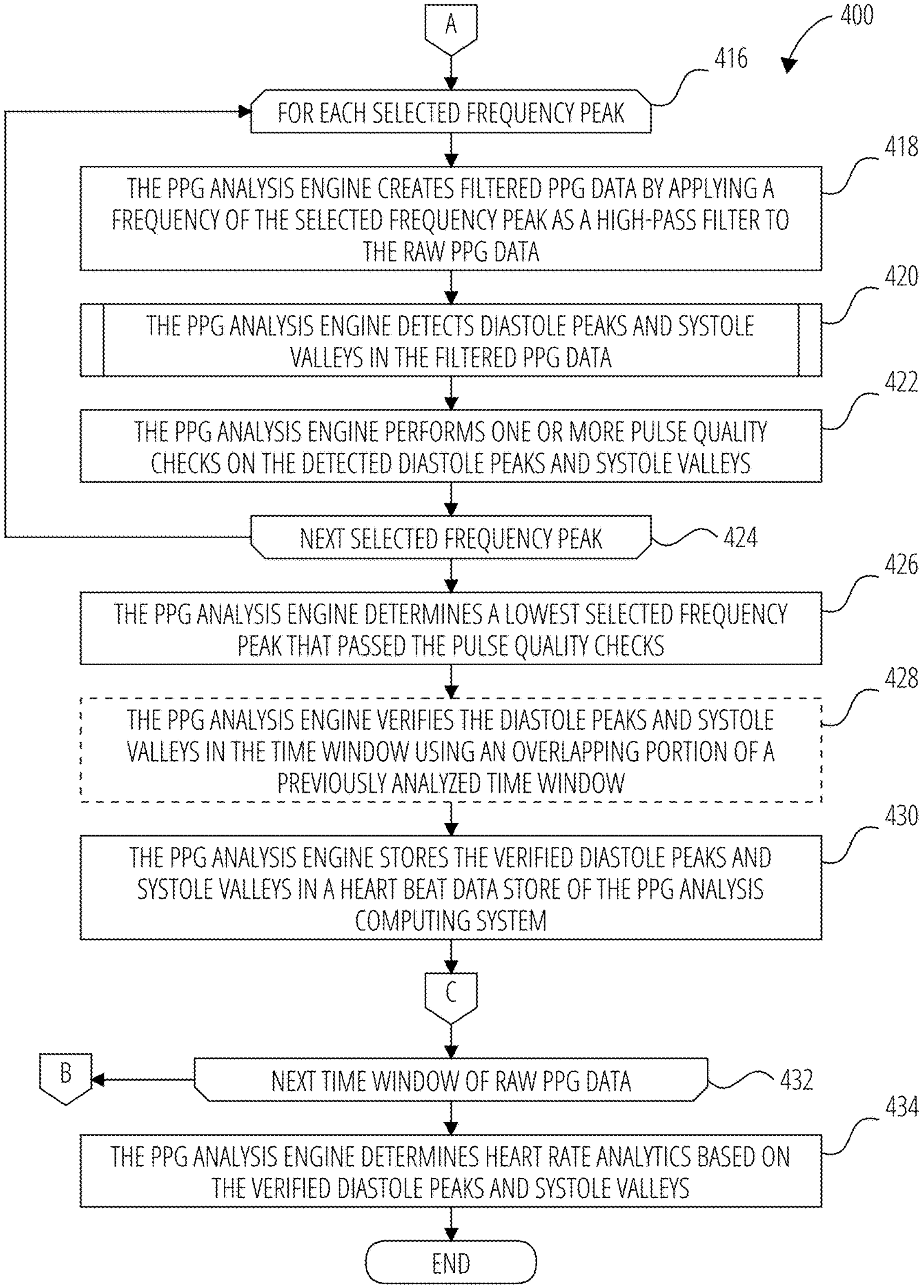

FIG. 4A-FIG. 4B are a flowchart that illustrates a non-limiting example embodiment of a method of measuring heart rate analytics using raw PPG data according to various aspects of the present disclosure.

From a start block, the method 400 proceeds to block 402, where a wearable PPG sensor 204 generates raw PPG data. At block 404, a data collection engine 310 of a PPG analysis computing system 206 receives the raw PPG data generated by the wearable PPG sensor 204 and stores the raw PPG data in a PPG data store 308 of the PPG analysis computing system 206. In some embodiments, the method 400 may operate on the raw PPG data in a streaming fashion, such that once a certain amount of raw PPG data is received (e.g., a time window worth of raw PPG data), the method 400 may proceed to detect heart beats in the received raw PPG data without storing the raw PPG data in the PPG data store 308. However, by storing the raw PPG data in the PPG data store 308, the raw PPG data may be kept available for future analysis.

The method 400 then advances to a for-loop defined between a for-loop start block 406 and a for-loop end block 432, where a time window of the raw PPG data is processed. Any suitable size of time window may be used. Using a time window that is not too large may improve the accuracy of the detected heart beats, at least because the method 400 includes adaptive removal of non-pulsatile signals. If such non-pulsatile signals are changing over time, then running the pulse detector over smaller windows may allow the method 400 to more accurately track changes in non-pulsatile signals and therefore remove them more effectively. In some embodiments, the size for the time window may be in a range from 8 seconds to 12 seconds, such as 10 seconds.

From the for-loop start block 406, the method 400 advances to block 408, where a PPG analysis engine 314 of the PPG analysis computing system 206 performs one or more signal quality checks on the raw PPG data. While the method 400 is robust to some categories of motion-related artifacts, it is known to those of skill in the art that intense motion can cause meaningless raw PPG data to be generated. Accordingly, the signal quality checks may determine whether the raw PPG data should even be considered valid, or whether it is too corrupted by intense motion to be usable. In some embodiments, data from a motion sensor may be used to detect relatively large amounts of motion, and if a relatively large amount of motion is detected, the signal quality check may fail. In some embodiments, a technique for distinguishing rest states from active states may be used, and the signal quality check may fail if the raw PPG data is determined to be associated with an active state.

In some embodiments, additional signal quality checks may be applied even if intense motion is not detected. For example, a quality estimate may be determined based on one or more of a signal to noise ratio (SNR) of the raw PPG data, an entropy of the raw PPG data, a correlation between detected pulses, or kurtosis of the power spectral density (PSD). Each of these values may be compared to an acceptable range of values, and the signal quality check may fail if one or more of the values are outside of their acceptable range.

The method 400 then proceeds to a decision block 410. If it was determined that the one or more signal quality checks failed, then the result of decision block 410 is NO, and the method 400 proceeds to a continuation terminal ("terminal C") to reach the end of the for-loop and process the next time window of raw PPG data. Otherwise, if it was determined that the one or more signal quality checks passed, then the result of decision block 410 is YES, and the method 400 proceeds to block 412.

Before attempting to detect heart beats in raw PPG data, a helpful preprocessing step is to high-pass filter the raw PPG data to remove low frequency content originating from sources such as respiration, baseline drift in the raw PPG data, low frequency motion artifacts, Mayer waves, and other low frequency content. This filtering isolates the pulsatile component of the raw PPG data, making heart beat detection easier and more accurate. However, in the presence of non-pulsatile artifacts, automatically choosing an appropriate frequency for the high-pass filter becomes challenging as the appropriate frequency depends on the type of artifacts present, which is typically not known beforehand. In previous techniques, a static frequency cutoff around 0.2-0.3 Hz is almost universally used to attempt to remove physiology-related low frequency content (e.g., respiration, Mayer waves, etc.). However, if a static 0.2-0.3 Hz cutoff is used, some low frequency artifacts may still be present and accurate heart beat detection may be compromised. In the method 400, an adaptive technique is used to choose an appropriate frequency cutoff that removes low frequency motion artifacts that are actually present in the raw PPG data instead of relying on a predetermined static cutoff frequency.

Accordingly, at block 412, the PPG analysis engine 314 determines a plurality of frequency peaks in the raw PPG data using a Fourier analysis. The frequency corresponding to the heart beat signal shows up as a peak in the Fourier spectrum. However, there may be several other peaks present in the Fourier spectrum from other sources (e.g., respiration, Mayer waves, arm swinging, etc.). In some embodiments, low frequency components may be suppressed by taking the derivative of the Fourier spectrum up to a cut-off frequency. Any suitable cut-off frequency may be used, including but not limited to cut-off frequencies selected from a range of 0.8 Hz to 1.3 Hz, such as 1.2 Hz.

At block 414, the PPG analysis engine 314 determines a plurality of selected frequency peaks from the plurality of frequency peaks. If the derivative of the Fourier spectrum was used to suppress low frequency components, the plurality of selected frequency peaks may be determined from the derivative of the Fourier transform.

Any suitable technique may be used for determining the selected frequency peaks. In some embodiments, one or more selection criteria may be used to exclude peaks that likely arise from non-pulsatile sources such as noise or periodic motion artifacts.

One non-limiting example of a selection criterion is a physiologically plausible range for a heart beat frequency. For example, frequencies below 30 beats per minute (0.5 Hz) and above 300 beats per minute (5 Hz) are physiologically unlikely to correspond to a heart rate. Frequency peaks outside of this range are therefore not likely to represent heart beats and would be considered to fail this selection criterion. The frequencies of 0.5 Hz and 300 Hz are non-limiting examples of a physiologically plausible range for heart beat frequencies, and in some embodiments, different thresholds for the physiologically plausible range for heart beat frequencies may be used. For example, in some embodiments, suitable thresholds may be determined based on characteristics of the subject 202, including but not limited to an age of the subject 202 or previously measured heart rate information from the subject 202.

Another non-limiting example of a selection criterion is a minimum amplitude threshold. For example, after determining an amplitude of the largest peak in the Fourier spectrum between minimum and maximum threshold frequencies (e.g., the minimum and maximum frequencies of the physiologically plausible range described above), peaks that are not larger than a predetermined fraction of the amplitude of the largest peak may fail the selection criterion. In some embodiments, the predetermined fraction may be selected from a range of 25%-35%, such as 30%.

Yet another non-limiting example of a selection criterion is a range between a valid minimum and maximum for a full width at half maximum (FWHM) value for the peak. This selection criterion may help avoid selection of peaks that are unrealistically narrow or broad, such as broad peaks that may arise from sudden motion. In some embodiments, the valid minimum width may be selected from a range of 0.09 Hz-0.11 Hz, such as 0.10 Hz. In some embodiments, the valid maximum width may be selected from a range of 0.39 Hz to 0.41 Hz, such as 0.40 Hz.

The method 400 then proceeds to a continuation terminal ("terminal A"). From terminal A (FIG. 4B), the method 400 proceeds to a for-loop defined between a for-loop start block 416 and a for-loop end block 424, wherein the raw PPG data is processed using each of the selected frequency peaks. In some embodiments, the loops of the for-loop may be performed in series, such that each selected frequency peak is considered separately. In some embodiments, the loops of the for-loop may be performed at least partially concurrently, such that two or more selected frequency peaks are processed at least partially concurrently in order to reduce the overall time for the execution of the for-loop.

Any suitable number of frequency peaks may be selected and processed through the for-loop. In some embodiments, a predetermined number of frequency peaks may be selected by block 414 for processing in the for-loop. In some embodiments, a set of valid frequency peaks may be determined in block 414, and the for-loop may process the frequency peaks of the set of valid frequency peaks in order of increasing frequency until a frequency peak that passes the pulse quality checks of block 422 is found, at which point the for-loop terminates without processing the rest of the valid frequency peaks. While this dynamic processing of an indeterminate number of selected frequency peaks may be flexible, it has been found that processing a predetermined number of three peaks is an optimal number of selected peaks to consider and provides adequate results. In other embodiments, another predetermined number of selected frequency peaks may be processed.

From for-loop start block 416, the method 400 advances to block 418, where the PPG analysis engine 314 creates filtered PPG data by applying a frequency of the selected frequency peak as a high-pass filter to the raw PPG data. The resulting filtered PPG data has been cleaned of low-frequency noise that is likely to represent motion or other low-frequency artifacts in the raw PPG data.

Figure 5:
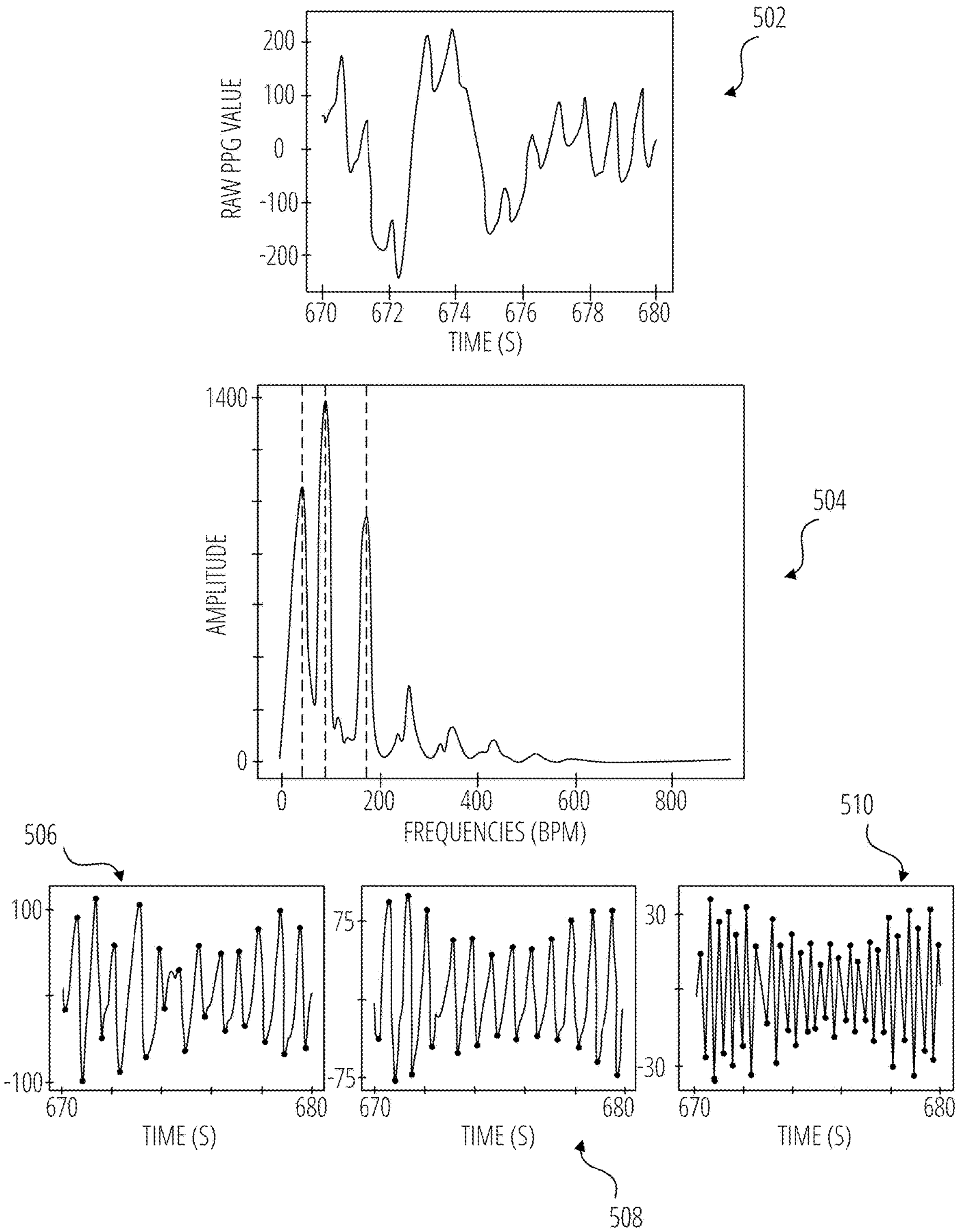
FIG. 5 includes charts that provide a non-limiting example illustration of the processing of raw PPG data to create filtered PPG data using three selected frequency peaks, according to various aspects of the present disclosure.

FIG. 5 includes charts that provide a non-limiting example illustration of the processing of raw PPG data to create filtered PPG data using three selected frequency peaks, according to various aspects of the present disclosure. A top chart illustrates raw PPG data 502, which, though it includes a plurality of peaks and valleys, it is clear from the varying amplitudes of the peaks and valleys that the measured signal includes noise from various sources. At block 412, the PPG analysis engine 314 conducts a Fourier analysis on the raw PPG data 502 to generate the Fourier spectrum 504 illustrated in the middle of FIG. 5. As can be seen, there are several high-amplitude peaks within the Fourier spectrum 504, and three of the high amplitude peaks, illustrated with dotted lines, are selected at block 414. An example of applying the frequencies of these selected peaks as a high-pass filter to the raw PPG data 502 is illustrated in the first chart 506, the second chart 508, and the third chart 510 at the bottom of FIG. 5. It is shown in these charts that the different selected frequencies provide different results that may not eliminate enough noise (e.g., first chart 506) or may convert too much noise to signal peaks (e.g., third chart 510). Techniques for selecting a desired frequency peak from these selected frequency peak that is expected to represent the heart beat signal and provide the best filter performance are discussed below.

Returning to FIG. 4B, the method 400 then advances to subroutine block 420, where a subroutine is executed in which the PPG analysis engine 314 detects diastole peaks and systole valleys in the filtered PPG data. Any suitable technique may be used to detect the diastole peaks and systole valleys in the filtered PPG data, including but not limited to the subroutine 600 illustrated in FIG. 6A-FIG. 6B and described in detail below. In some embodiments, the diastole peaks and systole valleys may be returned from the subroutine as a time series of peak-valley pairs that each represent a pulse or heart beat, or in any other suitable format.

At block 422, the PPG analysis engine 314 performs one or more pulse quality checks on the detected diastole peaks and systole valleys. The pulse quality checks may include one or more checks to determine, based on their characteristics, whether each peak-valley pair is likely to represent a pulse or heart beat, or is likely to represent an artifact. In some embodiments, the selected frequency peak may be determined to pass the one or more pulse quality checks if all pulse quality checks pass for all of the peak-valley pairs detected within the filtered PPG data, and may be determined to fail the one or more pulse quality checks if any of the pulse quality checks fail for any of the peak-valley pairs. In some embodiments, a tolerance threshold of a predetermined number of peak-valley pairs that may fail the pulse quality checks may be used to allow one or more peak-valley pairs to fail the pulse quality checks without failing the entire selected frequency peak.

In some embodiments, the pulse quality checks may include one or more checks based on time intervals between peaks, between valleys, and/or between peaks and valleys. For example, since the peak-peak interval represents the amount of time between heart beats, similar thresholds to the physiologically plausible heart rate thresholds described above may be used. That is, a minimum time interval of 0.2 seconds would represent a heart rate of 300 bpm, and a maximum time interval of 2 seconds would represent a heart rate of 30 bpm. These values were described above as non-limiting examples of boundaries of physiologically plausible heart rates for selecting frequency peaks. A similar range may be used for the pulse quality check, in that a peak-peak interval less than 0.2 seconds or greater than 2 seconds may be determined to be unlikely to be physiologically plausible, and would fail the pulse quality check. As another example, since the peak-valley interval represents the time between diastole and systole in the cardiac cycle, the valley is physiologically expected to follow fairly soon after the peak. As such, the pulse quality checks may include a maximum time interval between a peak and the ensuing valley, such as 0.6 seconds (or another suitable value). As yet another example, the characteristics of the rate of change of the peak-peak intervals, valley-valley intervals, and/or peaks and valleys may be examined. For example, a predetermined percentile (e.g., a percentile selected from a range of the 93rd percentile to the 98th percentile, such as the 95th percentile) of the rate of change between consecutive time intervals may be compared to a predetermined threshold value. If the predetermined percentile does not meet the predetermined threshold, the pulse quality check may fail.

In some embodiments, the pulse quality checks may include one or more checks based on peak-to-valley amplitudes. For valid peak-valley pairs, there is expected to be a relatively large amplitude between the peak and the valley, which is ensured by these checks. Such checks may include one or more of a minimum amplitude threshold, a maximum amplitude threshold, a threshold for the maximum of the largest amplitude divided by the mean amplitude, or other suitable thresholds. In some embodiments, a predetermined percentile (e.g., a percentile selected from a range of the 93rd percentile to the 98th percentile, such as the 95th percentile) of the rate of change of the peak-to-valley amplitudes may be compared to a predetermined threshold value, with the predetermined percentile failing to meet the predetermined threshold considered as failing the pulse quality check. In some embodiments, the amplitudes may be measured between a peak and the subsequent valley, and/or may be measured between a valley and the subsequent peak.

The method 400 then advances to the for-loop end block 424. If further selected frequency peaks remain to be processed, then the method 400 returns to for-loop start block 416 to process the next selected frequency peak. Otherwise, if all of the selected frequency peaks have been processed, then the method 400 advances from the for-loop end block 424 to block 426.

At block 426, the PPG analysis engine 314 determines a lowest selected frequency peak that passed the pulse quality checks. This lowest selected frequency peak is then used as the filter frequency peak, and the diastolic peaks and systolic valleys determined using that filter frequency peak (e.g., from subroutine block 420) are used in the subsequent analysis. In some embodiments if there is adequate memory for storage, the peak-valley pairs determined at subroutine block 420 may be stored after being returned from the subroutine to avoid having to recompute the peak-valley pairs, and may be used moving forward while deleting peak-valley pairs determined for other selected frequency peaks. In some embodiments, the peak-valley pairs may not be retained after the for-loop moves on to the next selected frequency peak, and once a frequency peak is chosen as the filter frequency peak, the subroutine of subroutine block 420 may be executed again to recompute the peak-valley pairs in order to reduce the memory burden of saving copies of the peak-valley pairs for each of the selected frequency peaks.

At optional block 428, the PPG analysis engine 314 verifies the diastole peaks and systole valleys in the time window using an overlapping portion of a previously analyzed time window. In some embodiments, the method 400 may process the raw PPG data in streaming fashion. For example, the for-loop may process the time window of raw PPG data (for example, 10 seconds of raw PPG data) to find the peak-valley pairs within that time window, and then move the window forward by a stride length that is less than the size of the window (for example, 2 seconds) for a subsequent iteration of the for-loop. This allows for a consistency check: if matching peak-valley pairs are found in overlapping portions of the time window, this provides additional confidence that the matching peak-valley pairs are valid and do not represent artifacts. Conversely, if a peak-valley pair is found in one time window that is not found in an overlapping portion of another time window, then the non-matching peak-valley pair may be more likely to represent an artifact, and may be removed from one of (or both of) the time windows. Optional block 428 is described as optional because, in some embodiments, the stride length of the time window may be the same as or greater than the size of the time window, and so there may not be overlapping portions to compare. Also, for a first iteration of the for-loop, there may not yet be peak-valley pairs from another time window for comparison.

The method 400 then advances to block 430, where the PPG analysis engine 314 stores the verified diastole peaks and systole valleys in the heart beat data store 312. The method 400 then proceeds through terminal C to the for-loop end block 432. If further time windows of raw PPG data remain to be processed, then the method 400 returns via a continuation terminal ("terminal B") to the for-loop start block 406 to process the next time window. Otherwise, the method 400 advances from the for-loop end block 432 to block 434.

At block 434, the PPG analysis engine 314 determines heart rate analytics based on the verified diastole peaks and systole valleys. Since the peak-valley pairs are highly accurate despite the generally low reliability of data generated by wearable PPG sensors 204, many types of heart rate analytics can reliably be calculated from the peak-valley pairs determined by the method 400. For example, interbeat intervals (IBI), or the time difference between consecutive peaks in seconds, may be used to generate various heart rate analytics. One simple analytic is heart rate, which may be defined as:

$$\text{Heart Rate} = \frac{60}{\text{mean}(IBI)}$$

Alternatively, heart rate may be defined as:

$$\text{Heart Rate} = \frac{60}{\text{median}(IBI)}$$

to provide additional robustness with respect to outliers.

Another example of a heart rate analytic that may be generated based on the peak-valley pairs generated by the method 400 is heart rate variability (HRV). HRV measures beat-to-beat variability in heart rate. More precisely, in some embodiments, HRV is measured using the root mean square of successive differences (RMSSD):

$$RMSSD = \sqrt{\left(\frac{1}{N-1}\right)\sum_{i=0}^{N-2}(IBI_{i+1} - IBI_i)^2}$$

HRV is typically measured over a period of time. The IBIs collected over that period of time are input into the RMSSD formula to obtain HRV. The window of time may be short, such as between one minute and five minutes, or it can be long, such as over an entire rest period, overnight, or over an entire day. Heart rate variability is very sensitive to errors in the IBI values, and so the improved data generated by the method 400 is critical to enabling the generation of reliable HRV measurement. RMSSD is a non-limiting example of a measurement of HRV, and in other embodiments, other measurements of HRV may be calculated instead of and/or in addition to RMSSD, including but not limited to standard deviation of all normal IBIs (SDNN), standard deviation of time window averages of IBIs (SDANN), mean of the standard deviations of IBI intervals for time window averages for a period of time such as 24 hours (ASDNN index), a number of IBIs that differ by more than a threshold amount from a neighboring interval (NN50), a percentage of IBIs that differ by more than a threshold amount from a neighboring interval (pNN50), or a difference between IBIs at night and during the day.

The method 400 then proceeds to an end block and terminates.

Figure 6A:
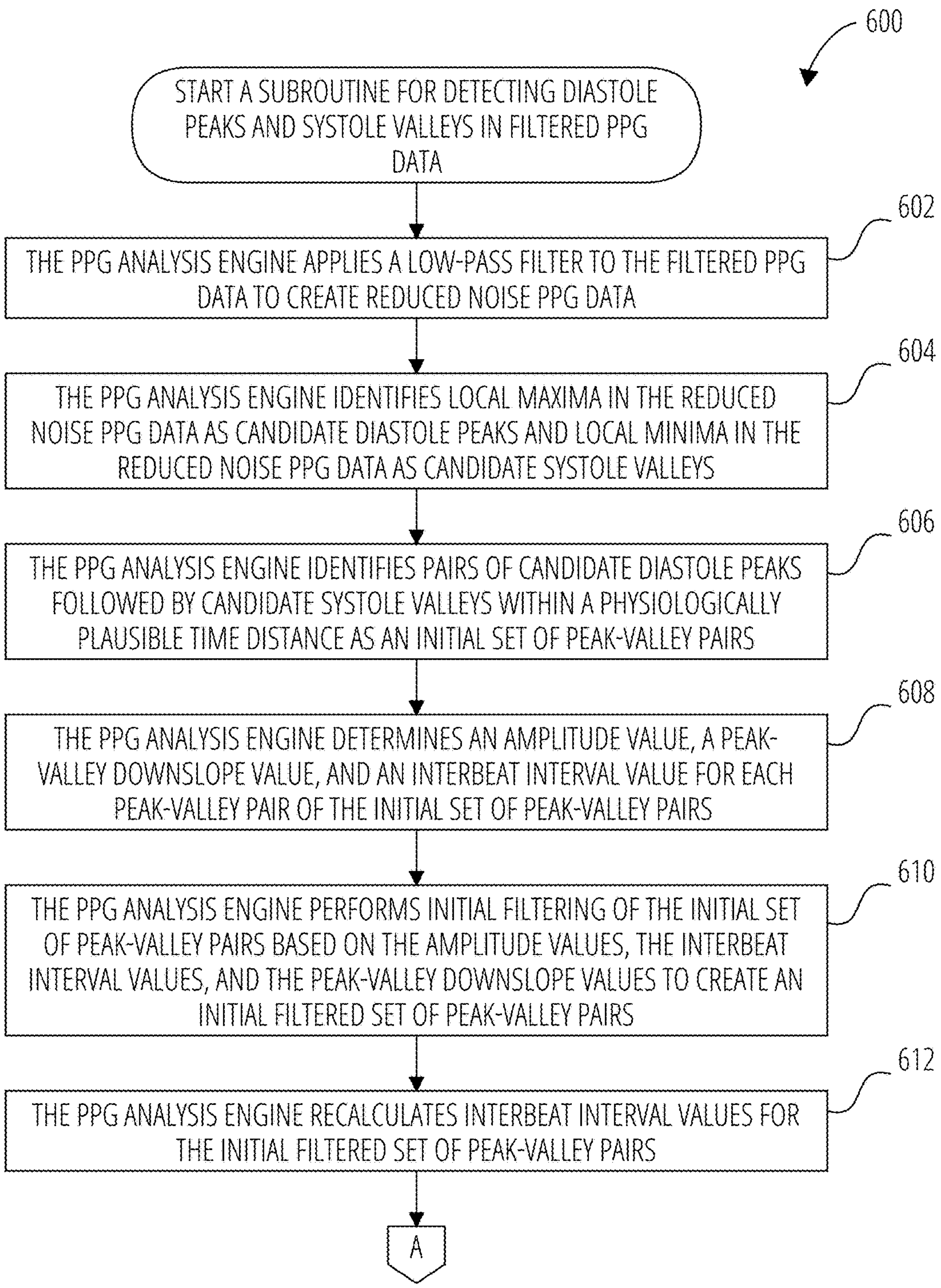
FIG. 6A-FIG. 6B are a flowchart that illustrates a non-limiting example embodiment of a subroutine for detecting diastole peaks and systole valleys in filtered PPG data according to various aspects of the present disclosure.
Figure 6B:
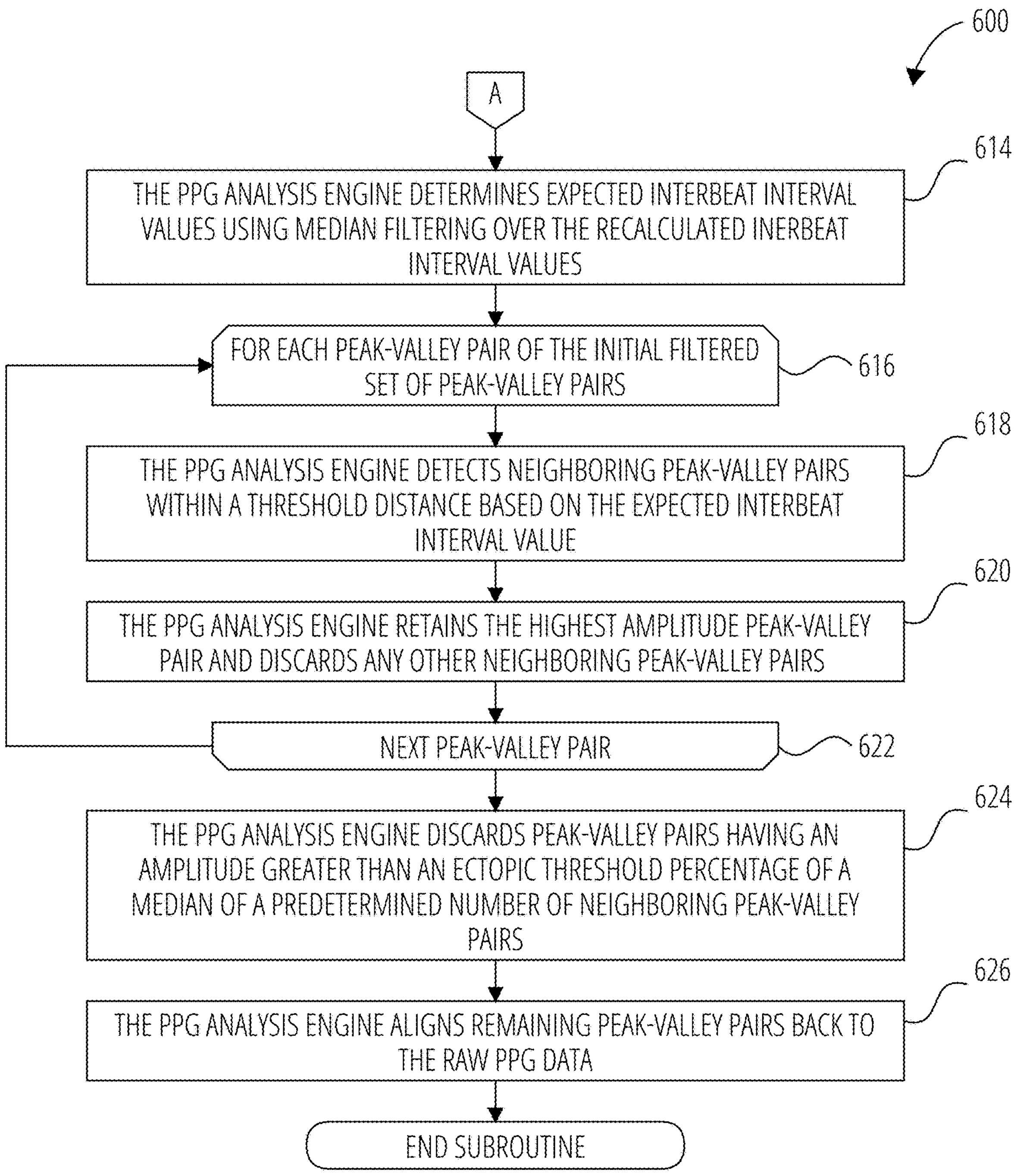

FIG. 6A-FIG. 6B are a flowchart that illustrates a non-limiting example embodiment of a subroutine for detecting diastole peaks and systole valleys in filtered PPG data according to various aspects of the present disclosure. The subroutine 600 is a non-limiting example of a subroutine suitable for use at subroutine block 420 of the method 400 described above. In the subroutine 600, it is assumed that a high-pass filter has been applied to raw PPG data, as described in block 418 of FIG. 4B. While the high-pass filter may be reasonably effective in removing low frequency artifacts, the subroutine 600 further improves the detection of diastole peaks and systole valleys in the raw PPG data by further removing reflected pulses and detecting ectopic pulses such as pre-ventricular contractions.

From a start block, the subroutine 600 advances to block 602, where the PPG analysis engine 314 applies a low-pass filter to the filtered PPG data to create reduced noise PPG data. Any suitable filter for removing high-frequency noise may be applied. In some embodiments, a Gaussian filter may be applied. In some embodiments, a low-pass filter with an appropriate cutoff frequency to filter out noise and non-pulsatile signals, such as 10 Hz, may be used.

At block 604, the PPG analysis engine 314 identifies local maxima in the reduced noise PPG data as candidate diastole peaks and local minima in the reduced noise PPG data as candidate systole valleys. Any suitable technique may be used to find the local maxima and local minima. Since techniques for finding local maxima and minima in a time series are known to those of ordinary skill in the art (e.g., the extrema( ) function in R, the find_peaks function from the signal module from SciPy in Python, etc.), they are not discussed in further detail here for the sake of brevity.

For valid pulses, physiology dictates that a systole valley should follow a diastole peak within a short amount of time. Accordingly, at block 606, the PPG analysis engine 314 identifies pairs of candidate diastole peaks followed by candidate systole valleys within a physiologically plausible time distance as an initial set of peak-valley pairs. In some embodiments, the physiologically plausible time distance may be selected from a range of 0.55 s to 0.65 s, such as 0.6 seconds.

At block 608, the PPG analysis engine 314 determines an amplitude value, a peak-valley downslope value, and an interbeat interval value for each peak-valley pair of the initial set of peak-valley pairs. The amplitude metric may measure a difference in amplitude of the raw PPG data between the location of the peak of the peak-valley pair and the location of the valley of the peak-valley pair. The peak-valley downslope metric may measure a slope between the diastole peak and the systolic valley, computed as the ratio of pulse amplitudes to corresponding peak-valley distances. In a valid pulse, this ratio is expected to be higher compared to ectopic pulses or reflected waves, as the rate of pressure increase during the systolic phase is rapid. The interbeat interval metric may measure a time distance from the peak of the peak-valley pair to the peak of a subsequent peak-valley pair.

At block 610, the PPG analysis engine 314 performs initial filtering of the initial set of peak-valley pairs based on the amplitude values, the interbeat interval values, and the peak-valley downslope values to create an initial filtered set of peak-valley pairs. In some embodiments, the PPG analysis engine 314 may compare the amplitude values, peak-valley downslope values, and/or interbeat interval values of each peak-valley pair to the corresponding values of the other peak-valley pairs to determine peak-valley pairs to filter out. By using a comparison of these metrics within the initial set of peak-valley pairs instead of to predetermined thresholds, this technique becomes robust to changes in sensors, different monitoring locations, and is otherwise self-calibrating.

With respect to the amplitude values, in some embodiments, a given percentile (e.g., a percentile selected from a range from the 85th to the 95th percentile, such as the 90th percentile) of all amplitudes in the initial filtered set of peak-valley pairs may be determined, and any peak-valley pair having an amplitude less than a threshold percentage (e.g., a percentage selected from a range from 3% to 7%, such as 5%) of the given percentile value may be filtered out. In some embodiments, any peak-valley pair having an amplitude less than a threshold percentage (e.g., a percentage selected from a range from 25% to 35%, such as 30%) of the median of three neighboring peak-valley pairs may be filtered out. These amplitude comparisons may help to filter out noisy spikes in the raw PPG data.

With respect to the interbeat interval values, in some embodiments, any peak-valley pair having an interbeat interval value less than a physiologically plausible value (e.g., less than a threshold interbeat interval selected from a range of 0.19 to 0.21, such as 0.20, indicating a heart rate of about 300 bpm), and also having an amplitude smaller than a previous pulse, and also having an amplitude smaller than a threshold percentage (e.g., a percentage selected from a range from 70% to 80%, such as 75%) of a median of the neighboring three peak-valley pairs is likely to represent a reflected wave instead of a valid heartbeat, and so may be filtered out.

With respect to the peak-valley downslope values, in some embodiments, any peak-valley pair having a peak-valley downslope value lesser than a threshold percentage of its two neighboring pulses (e.g., a percentage selected from a range from 30% to 40%, such as 35%) is likely to represent an ectopic peak or a reflected wave, and may be filtered out.

In some embodiments, combinations of these metric values may be used in order to avoid problems that may arise from the data collection modality. For example, it is known that characteristics of photoplethysmography data can change depending on the skin tone of the subject (e.g., darker skin tones can lead to lower amplitude values for valid pulses). To avoid these issues, the PPG analysis engine 314 may exclude peak-valley pairs that fail both the amplitude value check and the peak-valley downslope value check, and may allow peak-valley pairs that satisfy at least one of the amplitude value check or the peak-valley downslope value check to pass on to the interbeat interval value check.

The subroutine 600 then proceeds to a continuation terminal ("terminal A").

While the quality of the initial filtered set of peak-valley pairs has been improved compared to the initial set of peak-valley pairs, the initial filtered set of peak-valley pairs may still include ectopic pulses and leftover reflected pulses that were not removed by the previous filtering. In some embodiments, additional interbeat interval and amplitude based filtering may be performed to remove these additional sources of noise.

Since the filter at block 610 may have removed some of the peak-valley pairs from the initial set of peak-valley pairs, the interbeat interval values for the neighboring peak-valley pairs will be different since they were calculated based on the presence of the now-removed peak-valley pair. Accordingly, from terminal A (FIG. 6B), the subroutine 600 advances to block 612, where the PPG analysis engine 314 recalculates interbeat interval values for the initial filtered set of peak-valley pairs.

At block 614, the PPG analysis engine 314 determines expected interbeat interval values using median filtering over the recalculated interbeat interval values. The intuition is that interbeat interval values are not expected to change greatly over short windows of time, and so peak-valley pairs that are clustered closer than the expected interbeat interval time are likely to include at least one invalid peak-valley pair. Any suitable technique may be used for determining the expected interbeat interval value via median filtering. For example, a rolling window of a size selected from a range from 7 to 11, such as 9, may be used for the median filter.

The subroutine 600 then advances to a for-loop defined between a for-loop start block 616 and a for-loop end block 622, wherein each peak-valley pair of the initial filtered set of peak-valley pairs is reviewed to find any nearby peak-valley pairs that are likely to represent noise. From the for-loop start block 616, the subroutine 600 advances to block 618, where the PPG analysis engine 314 detects neighboring peak-valley pairs within a threshold distance based on the expected interbeat interval value. In some embodiments, the PPG analysis engine 314 may search for peak-valley pairs that are within a threshold distance from the given peak-valley pair being processed, wherein the threshold distance is shorter than the expected interbeat interval. For example, a threshold distance of a given percentage of the interbeat interval, wherein the given percentage is selected from a range of 50% to 70%, such as 60%, may be used. If any peak-valley pairs are present within that threshold distance (either before or after) the given peak, they may be identified at block 618.

At block 620, the PPG analysis engine 314 retains the highest amplitude peak-valley pair and discards any other neighboring peak-valley pairs. The rationale is that if peak-valley pairs are found much closer to a given peak-valley pair than its interbeat interval would indicate, they likely represent a reflection, and since reflections have smaller amplitudes than legitimate peak-valley pairs, retaining the highest amplitude peak-valley pair will remove all of the remaining reflections.

The subroutine 600 then advances to the for-loop end block 622. If further peak-valley pairs remain to be processed in the initial filtered set of peak-valley pairs, then the subroutine 600 returns to the for-loop start block 616 to process the next peak-valley pair. Otherwise, the subroutine 600 advances to block 624.

At block 624, the PPG analysis engine 314 discards peak-valley pairs having an amplitude greater than an ectopic threshold percentage of a median of a predetermined number of neighboring peak-valley pairs. Any suitable threshold may be used to detect ectopic peak-valley pairs. In some embodiments, the threshold may be selected from a range of 140% to 160%, such as 150%. In some embodiments, the predetermined number of peak-valley pairs to consider may be selected from a range of 4 to 6, such as 5. In some embodiments, the peak-valley pairs having amplitudes greater than the ectopic threshold percentage may be simply discarded. In some embodiments, the presence of an ectopic peak-valley pair may be recorded, either for its own analytics, or to discard the segment including the ectopic peak-valley pair from generating analytics that are undermined by the presence of ectopic peak-valley pairs.

After block 624, the remaining peak-valley pairs are considered to represent actual heart beats signified by the raw PPG data. However, because the locations of the remaining peak-valley pairs were determined using a smoothed version of the raw PPG data, they may not coincide exactly with the times of the actual peaks and valleys detected in the raw PPG data. Accordingly, at block 626, the PPG analysis engine 314 aligns remaining peak-valley pairs back to the raw PPG data. In some embodiments, this alignment may be performed by searching for local maxima or minima in the raw PPG data within an alignment threshold of the peaks or valleys, respectively, and adjusting the peaks and valleys to match the local maxima/minima. The alignment threshold is typically small—in some embodiments, an alignment threshold selected from a range of 0.11 s to 0.13 s, such as 0.12 s, may be used.

The subroutine 600 then advances to an end block and returns control to its caller.

In the preceding description, numerous specific details are set forth to provide a thorough understanding of various embodiments of the present disclosure. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The order in which some or all of the blocks appear in each method flowchart should not be deemed limiting. Rather, one of ordinary skill in the art having the benefit of the present disclosure will understand that actions associated with some of the blocks may be executed in a variety of orders not illustrated, or even in parallel.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

EXAMPLES

The following paragraphs provide non-limiting example embodiments of the present disclosure.

Example 1: A non-transitory computer-readable medium having logic stored thereon that, in response to execution by one or more processors of a computing system, causes the computing system to perform actions for measuring heart rate analytics using raw photoplethysmography (PPG) data, the actions comprising: determining, by the computing system, a plurality of frequency peaks in the raw PPG data using a Fourier analysis; determining, by the computing system, a plurality of selected frequency peaks from the plurality of frequency peaks; for each selected frequency peak of the plurality of selected frequency peaks: creating, by the computing system, filtered PPG data by applying a frequency of the selected frequency peak as a high-pass filter to the raw PPG data; detecting, by the computing system, diastole peaks and systole valleys in the filtered PPG data; and performing, by the computing system, one or more pulse quality checks on the detected diastole peaks and systole valleys; and using, by the computing system, diastole peaks and systole valleys associated with a lowest selected frequency peak that passed the pulse quality checks to determine a heart rate analytic measurement.

Example 2: The non-transitory computer-readable medium of example 1, wherein determining the plurality of selected frequency peaks includes selecting frequency peaks based on at least one selection criterion, wherein the at least one selection criterion includes at least one of: a physiologically plausible range for a heart beat frequency; a minimum amplitude threshold; or a range for a full width at half maximum (FWHM) value.

Example 3: The non-transitory computer-readable medium of any one of examples 1-2, wherein detecting the diastole peaks and systole valleys in the filtered PPG data includes: applying a low-pass filter to the filtered PPG data to create reduced noise PPG data; detecting a set of peak-valley pairs within the reduced noise PPG data; performing amplitude-based filtering and interbeat interval (IBI) based filtering on the detected set of peak-valley pairs to create a filtered set of peak-valley pairs; and aligning the filtered set of peak-valley pairs back to the raw PPG data.

Example 4: The non-transitory computer-readable medium of example 3, wherein performing amplitude-based filtering and IBI-based filtering includes initial filtering of at least one of: discarding peak-valley pairs having amplitudes less than a first threshold percentage of a 90th percentile of all peak-valley pair amplitudes or less than a second threshold percentage of a median of three neighboring peak-valley pairs; discarding peak-valley pairs having peak-valley downslope values less than a threshold percentage of its two neighboring peak-valley pairs; or discarding peak-valley pairs having an interbeat interval less than a physiologically plausible value, an amplitude smaller than a previous peak-valley pair, and an amplitude smaller than a third threshold percentage of a median of three neighboring peak-valley pairs.

Example 5: The non-transitory computer-readable medium of example 4, wherein performing amplitude-based filtering and IBI-based filtering further includes: recalculating interbeat intervals after discarding peak-valley pairs during the initial filtering; performing median filtering on the recalculated interbeat intervals to determine expected interbeat interval values; and for each peak-valley pair: detect neighboring peak-valley pairs within a threshold distance of the peak-valley pair, wherein the threshold distance is based on the expected interbeat interval value; and in response to detecting neighboring peak-valley pairs within the threshold distance of the peak-valley pair, retaining a highest amplitude peak-valley pair and discarding other peak-valley pairs.

Example 6: The non-transitory computer-readable medium of any one of examples 4-5, wherein performing amplitude-based filtering and IBI-based filtering further includes: discarding ectopic peak-valley pairs having an amplitude greater than an ectopic threshold percentage of a median of five neighboring peak-valley pairs.

Example 7: The non-transitory computer-readable medium of any one of examples 3-6, wherein aligning the filtered plurality of peak-valley pairs back to the raw PPG data includes: aligning peaks to a local maximum of the raw PPG data within an alignment threshold of the peak; and aligning valleys to a local minimum of the raw PPG data within the alignment threshold of the valley.

Example 8: The non-transitory computer-readable medium of any one of examples 1-7, wherein performing one or more pulse quality checks on the detected diastole peaks and systole valleys includes one or more of: determining whether at least one of peak-to-peak intervals, peak-to-valley intervals, or valley-to-peak intervals are within physiologically plausible ranges; determining whether a predetermined percentile of at least one of peak-to-peak intervals, peak-to-valley intervals, or valley-to-peak intervals meets a predetermined threshold; or determining whether peak-to-valley amplitudes meet an amplitude threshold.

Example 9: The non-transitory computer-readable medium of any one of examples 1-8, wherein the PPG data is generated by a peripherally worn sensor.

Example 10: The non-transitory computer-readable medium of any one of examples 1-9, wherein the heart rate analytic is a heart rate variability.

Example 11: A computer-implemented method of measuring heart rate analytics using raw photoplethysmography (PPG) data, the method comprising: determining, by a computing system, a plurality of frequency peaks in the raw PPG data using a Fourier analysis; determining, by the computing system, a plurality of selected frequency peaks from the plurality of frequency peaks; for each selected frequency peak of the plurality of selected frequency peaks: creating, by the computing system, filtered PPG data by applying a frequency of the selected frequency peak as a high-pass filter to the raw PPG data; detecting, by the computing system, diastole peaks and systole valleys in the filtered PPG data; and performing, by the computing system, one or more pulse quality checks on the detected diastole peaks and systole valleys; and using, by the computing system, diastole peaks and systole valleys associated with a lowest selected frequency peak that passed the pulse quality checks to determine a heart rate analytic measurement.

Example 12: The computer-implemented method of example 11, wherein determining the plurality of selected frequency peaks includes selecting frequency peaks based on at least one selection criterion, wherein the at least one selection criterion includes at least one of: a physiologically plausible range for a heart beat frequency; a minimum amplitude threshold; or a range for a full width at half maximum (FWHM) value.

Example 13: The computer-implemented method of any one of examples 11-12, wherein detecting the diastole peaks and systole valleys in the filtered PPG data includes: applying a low-pass filter to the filtered PPG data to create reduced noise PPG data; detecting a set of peak-valley pairs within the reduced noise PPG data; performing amplitude-based filtering and interbeat interval (IBI) based filtering on the detected set of peak-valley pairs to create a filtered set of peak-valley pairs; and aligning the filtered set of peak-valley pairs back to the raw PPG data.

Example 14: The computer-implemented method of example 13, wherein performing amplitude-based filtering and IBI-based filtering includes initial filtering of at least one of: discarding peak-valley pairs having amplitudes less than a first threshold percentage of a 90th percentile of all peak-valley pair amplitudes or less than a second threshold percentage of a median of three neighboring peak-valley pairs; discarding peak-valley pairs having peak-valley downslope values less than a threshold percentage of its two neighboring peak-valley pairs; or discarding peak-valley pairs having an interbeat interval less than a physiologically plausible value, an amplitude smaller than a previous peak-valley pair, and an amplitude smaller than a third threshold percentage of a median of three neighboring peak-valley pairs.

Example 15: The computer-implemented method of example 14, wherein performing amplitude-based filtering and IBI-based filtering further includes: recalculating interbeat intervals after discarding peak-valley pairs during the initial filtering; performing median filtering on the recalculated interbeat intervals to determine expected interbeat interval values; and for each peak-valley pair: detect neighboring peak-valley pairs within a threshold distance of the peak-valley pair, wherein the threshold distance is based on the expected interbeat interval value; and in response to detecting neighboring peak-valley pairs within the threshold distance of the peak-valley pair, retaining a highest amplitude peak-valley pair and discarding other peak-valley pairs.

Example 16: The computer-implemented method of any one of examples 14-15, wherein performing amplitude-based filtering and IBI-based filtering further includes: discarding ectopic peak-valley pairs having an amplitude greater than an ectopic threshold percentage of a median of five neighboring peak-valley pairs.

Example 17: The computer-implemented method of any one of examples 13-16, wherein aligning the filtered plurality of peak-valley pairs back to the raw PPG data includes: aligning peaks to a local maximum of the raw PPG data within an alignment threshold of the peak; and aligning valleys to a local minimum of the raw PPG data within the alignment threshold of the valley.

Example 18: The computer-implemented method of any one of examples 11-17, wherein performing one or more pulse quality checks on the detected diastole peaks and systole valleys includes one or more of: determining whether at least one of peak-to-peak intervals, peak-to-valley intervals, or valley-to-peak intervals are within physiologically plausible ranges; determining whether a predetermined percentile of at least one of peak-to-peak intervals, peak-to-valley intervals, or valley-to-peak intervals meets a predetermined threshold; or determining whether peak-to-valley amplitudes meet an amplitude threshold.

Example 19: The computer-implemented method of any one of examples 11-18, wherein the PPG data is generated by a peripherally worn sensor.

Example 20: The computer-implemented method of any one of examples 11-19, wherein the heart rate analytic is a heart rate variability.

What is claimed is:

1. A non-transitory computer-readable medium having logic stored thereon that, in response to execution by one or more processors of a computing system, causes the computing system to perform actions for measuring heart rate analytics using raw photoplethysmography (PPG) data, the actions comprising:

determining, by the computing system, a plurality of frequency peaks in the raw PPG data using a Fourier analysis;

selecting, by the computing system, a plurality of selected frequency peaks from the plurality of frequency peaks based on at least one selection criterion, wherein the at least one selection criterion includes at least one of a physiologically plausible range for a heart beat frequency, a minimum amplitude threshold for the frequency peak, or a range between a valid minimum and maximum for a full width at half maximum (FWHM) value for the frequency peak;

for each selected frequency peak of the plurality of selected frequency peaks:

creating, by the computing system, filtered PPG data by applying a frequency of the selected frequency peak as a high-pass filter to the raw PPG data;

detecting, by the computing system, diastole peaks and systole valleys in the filtered PPG data; and performing, by the computing system, one or more pulse quality checks on the detected diastole peaks and systole valleys, wherein the performing one or more pulse quality checks on the detected diastole peaks and systole valleys includes one or more of:

determining whether at least one of peak-to-peak intervals, peak-to-valley intervals, or valley-to-peak intervals are within physiologically plausible ranges;

determining whether a predetermined percentile of at least one of peak-to-peak intervals, peak-to-valley intervals, or valley-to-peak intervals meets a predetermined threshold; or determining whether peak-to-valley amplitudes meet an amplitude threshold; and using, by the computing system, diastole peaks and systole valleys associated with a lowest selected frequency peak that passed the pulse quality checks to determine a heart rate analytic measurement, wherein the heart rate analytic measurement is a heart rate or a heart rate variability.

2. The non-transitory computer-readable medium of claim 1, wherein detecting the diastole peaks and systole valleys in the filtered PPG data includes:

applying a low-pass filter to the filtered PPG data to create reduced noise PPG data;

detecting a set of peak-valley pairs within the reduced noise PPG data;

performing amplitude-based filtering and interbeat interval (IBI) based filtering on the detected set of peak-valley pairs to create a filtered set of peak-valley pairs; and aligning the filtered set of peak-valley pairs back to the raw PPG data.

3. The non-transitory computer-readable medium of claim 2, wherein performing amplitude-based filtering and IBI-based filtering includes initial filtering of at least one of:

discarding peak-valley pairs having amplitudes less than a first threshold percentage of a 90th percentile of all peak-valley pair amplitudes or less than a second threshold percentage of a median of three neighboring peak-valley pairs;

discarding peak-valley pairs having peak-valley downslope values less than a threshold percentage of its two neighboring peak-valley pairs; or discarding peak-valley pairs having an interbeat interval less than a physiologically plausible value, an amplitude smaller than a previous peak-valley pair, and an amplitude smaller than a third threshold percentage of a median of three neighboring peak-valley pairs.

4. The non-transitory computer-readable medium of claim 3, wherein performing amplitude-based filtering and IBI-based filtering further includes:

recalculating interbeat intervals after discarding peak-valley pairs during the initial filtering;

performing median filtering on the recalculated interbeat intervals to determine expected interbeat interval values; and for each peak-valley pair:

detect neighboring peak-valley pairs within a threshold distance of the peak-valley pair, wherein the threshold distance is based on the expected interbeat interval value; and in response to detecting neighboring peak-valley pairs within the threshold distance of the peak-valley pair, retaining a highest amplitude peak-valley pair and discarding other peak-valley pairs.

5. The non-transitory computer-readable medium of claim 3, wherein performing amplitude-based filtering and IBI-based filtering further includes:

discarding ectopic peak-valley pairs having an amplitude greater than an ectopic threshold percentage of a median of five neighboring peak-valley pairs.

6. The non-transitory computer-readable medium of claim 2, wherein aligning the filtered plurality of peak-valley pairs back to the raw PPG data includes:

aligning peaks to a local maximum of the raw PPG data within an alignment threshold of the peak; and aligning valleys to a local minimum of the raw PPG data within the alignment threshold of the valley.

7. The non-transitory computer-readable medium of claim 1, wherein the PPG data is generated by a peripherally worn sensor.

8. A computer-implemented method of measuring heart rate analytics using raw photoplethysmography (PPG) data, the method comprising:

determining, by a computing system, a plurality of frequency peaks in the raw PPG data using a Fourier analysis;

selecting, by the computing system, a plurality of selected frequency peaks from the plurality of frequency peaks based on at least one selection criterion, wherein the at least one selection criterion includes at least one of a physiologically plausible range for a heart beat frequency, a minimum amplitude threshold for the frequency peak, or a range between a valid minimum and maximum for a full width at half maximum (FWHM) value for the frequency peak;

for each selected frequency peak of the plurality of selected frequency peaks:

creating, by the computing system, filtered PPG data by applying a frequency of the selected frequency peak as a high-pass filter to the raw PPG data;

detecting, by the computing system, diastole peaks and systole valleys in the filtered PPG data; and performing, by the computing system, one or more pulse quality checks on the detected diastole peaks and systole valleys, wherein the performing one or more pulse quality checks on the detected diastole peaks and systole valleys includes one or more of:

determining whether at least one of peak-to-peak intervals, peak-to-valley intervals, or valley-to-peak intervals are within physiologically plausible ranges;

determining whether a predetermined percentile of at least one of peak-to-peak intervals, peak-to-valley intervals, or valley-to-peak intervals meets a predetermined threshold; or determining whether peak-to-valley amplitudes meet an amplitude threshold; and using, by the computing system, diastole peaks and systole valleys associated with a lowest selected frequency peak that passed the pulse quality checks to determine a heart rate analytic measurement, wherein the heart rate analytic measurement is a heart rate or a heart rate variability.

9. The computer-implemented method of claim 8, wherein detecting the diastole peaks and systole valleys in the filtered PPG data includes:

applying a low-pass filter to the filtered PPG data to create reduced noise PPG data;

detecting a set of peak-valley pairs within the reduced noise PPG data;

performing amplitude-based filtering and interbeat interval (IBI) based filtering on the detected set of peak-valley pairs to create a filtered set of peak-valley pairs; and aligning the filtered set of peak-valley pairs back to the raw PPG data.

10. The computer-implemented method of claim 9, wherein performing amplitude-based filtering and IBI-based filtering includes initial filtering of at least one of:

discarding peak-valley pairs having amplitudes less than a first threshold percentage of a 90th percentile of all peak-valley pair amplitudes or less than a second threshold percentage of a median of three neighboring peak-valley pairs;

discarding peak-valley pairs having peak-valley downslope values less than a threshold percentage of its two neighboring peak-valley pairs; or discarding peak-valley pairs having an interbeat interval less than a physiologically plausible value, an amplitude smaller than a previous peak-valley pair, and an amplitude smaller than a third threshold percentage of a median of three neighboring peak-valley pairs.

11. The computer-implemented method of claim 10, wherein performing amplitude-based filtering and IBI-based filtering further includes:

recalculating interbeat intervals after discarding peak-valley pairs during the initial filtering;

performing median filtering on the recalculated interbeat intervals to determine expected interbeat interval values; and for each peak-valley pair:

detect neighboring peak-valley pairs within a threshold distance of the peak-valley pair, wherein the threshold distance is based on the expected interbeat interval value; and in response to detecting neighboring peak-valley pairs within the threshold distance of the peak-valley pair, retaining a highest amplitude peak-valley pair and discarding other peak-valley pairs.

12. The computer-implemented method of claim 10, wherein performing amplitude-based filtering and IBI-based filtering further includes:

discarding ectopic peak-valley pairs having an amplitude greater than an ectopic threshold percentage of a median of five neighboring peak-valley pairs.

13. The computer-implemented method of claim 9, wherein aligning the filtered plurality of peak-valley pairs back to the raw PPG data includes:

aligning peaks to a local maximum of the raw PPG data within an alignment threshold of the peak; and aligning valleys to a local minimum of the raw PPG data within the alignment threshold of the valley.

14. The computer-implemented method of claim 8, wherein the PPG data is generated by a peripherally worn sensor.

* * * * *